(12) United States Patent
Fouchard et al.

(10) Patent No.: US 9,933,380 B2
(45) Date of Patent: Apr. 3, 2018

(54) METHOD FOR IMAGING A MEDIUM THROUGH ELECTRICAL MEASUREMENTS WITH A CONTACT IMPEDANCE CORRECTION

(71) Applicants: Commissariat a L'Energie Atomique et aux Energies Alternatives, Paris (FR); Institut National de la Sante et de la Recherche Madicale (INSERM), Paris (FR)

(72) Inventors: Alexandre Fouchard, Grenoble (FR); Stephane Bonnett, Lyons (FR); Olivier David, Le Sappey (FR); Pascale Pham, Crolles (FR)

(73) Assignees: Commissariat à l'énergie atomique et aux énergies alternatives, Paris (FR); INSTITUT NATIONAL DE LA SANTE ET DE LA RECHERCHE MEDICALE (INSERM), Paris CEDEX 13 (FR)

( * ) Notice: Subject to any disclaimer, the term of this patent is extended or adjusted under 35 U.S.C. 154(b) by 104 days.

(21) Appl. No.: 14/953,153

(22) Filed: Nov. 27, 2015

(65) Prior Publication Data

US 2016/0153924 A1    Jun. 2, 2016

(30) Foreign Application Priority Data

Nov. 28, 2014 (FR) ...................................... 14 61677

(51) Int. Cl.
*G01R 27/04* (2006.01)
*G01R 27/32* (2006.01)
(Continued)

(52) U.S. Cl.
CPC ......... *G01N 27/026* (2013.01); *A61B 5/0536* (2013.01); *A61B 5/7203* (2013.01); *A61B 5/7271* (2013.01); *A61B 2562/04* (2013.01)

(58) Field of Classification Search
CPC .. G01N 27/026; A61B 5/0536; A61B 5/7271; A61B 5/7203; A61B 2562/04
(Continued)

(56) References Cited

U.S. PATENT DOCUMENTS 5,023,547 A * 6/1991 Pawlak ................... G01P 3/488
                                                    188/181 R
8,180,617 B1 * 5/2012 Klee ....................... G01N 27/00
                                                    702/19

(Continued)

FOREIGN PATENT DOCUMENTS

WO    WO 95/24155 A1    9/1995
WO    WO 98/23204 A1    6/1998

OTHER PUBLICATIONS

French Preliminary Search Report dated Jul. 15, 2015 in French Application 14 61677, filed Nov. 28, 2014 (with English Translation of Categories of Cited Documents).

(Continued)

*Primary Examiner* — Giovanni Astacio-Oquendo
(74) *Attorney, Agent, or Firm* — Oblon, McClelland, Maier & Neustadt, L.L.P.

(57) ABSTRACT

An EIT or differential EIT method in which measurements of voltage differences between electrodes are performed according to a measurement configuration in which at least one of the electrodes injecting a current in the medium being investigated is also used for performing a measurement of the voltage difference. The contact impedances of the different electrodes are measured thanks to a counter-electrode having a contact area with the medium much higher than the contact area of a unit electrode. The measurement of a (Continued)

contact impedance is performed by impedance spectroscopy by comparison with the impedance spectrum of an equivalent circuit. The contact impedances allow voltage drops in the injection electrodes to be calculated the voltage differences between these electrodes and to be corrected. Alternatively, the contact impedances can be used to correct or complete the direct model.

13 Claims, 11 Drawing Sheets

(51) Int. Cl.
    *G01N 27/02*    (2006.01)
    *A61B 5/053*    (2006.01)
    *A61B 5/00*     (2006.01)

(58) Field of Classification Search
    USPC .......................................... 324/647, 600, 629
    See application file for complete search history.

(56) References Cited

U.S. PATENT DOCUMENTS

| | | | |
|---|---|---|---|
| 9,053,785 B2* | 6/2015 | Krebs | G11C 13/0009 |
| 2009/0268505 A1* | 10/2009 | Beer | G11C 11/5614 |
| | | | 365/148 |
| 2010/0182827 A1* | 7/2010 | Kostylev | G11C 11/5678 |
| | | | 365/163 |
| 2011/0096594 A1* | 4/2011 | Franceschini | G11C 11/56 |
| | | | 365/163 |

OTHER PUBLICATIONS

Sunjoo Hong et al. "A 4.9 mΩ-Sensitivity Mobile Electrical Impedance Tomography IC for Early Breast-Cancer Detection System", IEEE Journal of Solid-State Circuits, vol. 50, No. 1, Jan. 1, 2015, 13 pages.

T. Vilhunen et al. "Detection of Faults in Resistive Coatings with an Impedance-Tomography-Related Approach", Measurement Science and Technology, vol. 13, 2002, 8 pages.

Eun Jung Lee et al. "Design of a Microscopic Electrical Impedance Tomography System for 3D Continuous Non-Destructive Monitoring of Tissue Culture", BioMedical Engineering Online, vol. 13, No. 142, 2014, 15 pages.

E. J. Woo et al. "Skin Impedance Measurements Using Simple and Compound Electrodes", 2200 Medical & Biological Engineering & Computing, vol. 30. No. 1, Jan. 1992, 6 pages.

Lasse M. Heikkinen et al. "Simultaneous Reconstruction of Electrode Contact Impedances and Internal Electrical Properties: II. Laboratory Experiments", Measurement Science and Technology, vol. 13, 2002, 7 pages.

J. K. Seo et al. "Nonlinear Inverse Problems in Imaging", Chapter 7: Electrical Impedance Tomography, First Edition, 2013, 55 pages.

Gregory Boverman et al. "Methods for Compensating for Variable Electrode Contact in EIT", IEEE Transactions on Biomedical Engineering, vol. 56, No. 12, Dec. 2009, 11 pages.

* cited by examiner

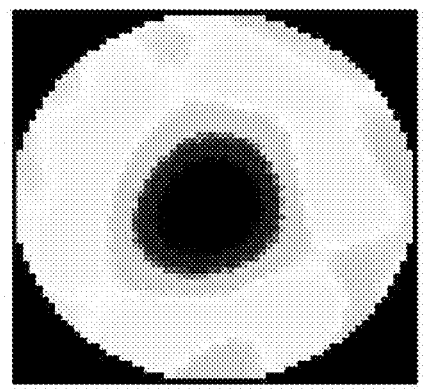 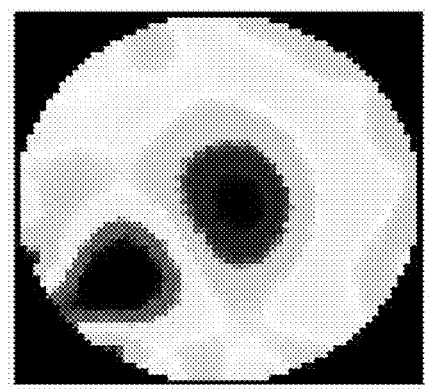
Fig. 12A　　　　　　　　Fig. 12B
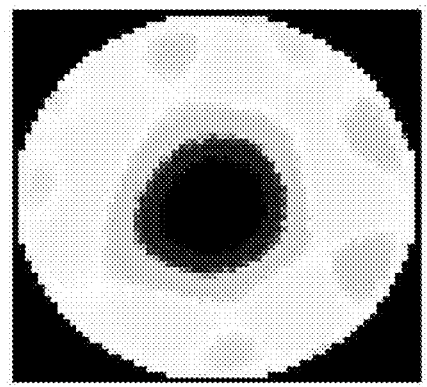 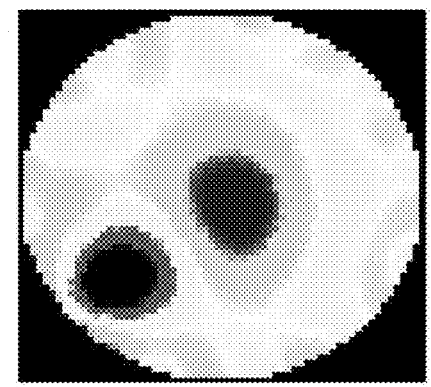
Fig. 13A　　　　　　　　Fig. 13B

METHOD FOR IMAGING A MEDIUM THROUGH ELECTRICAL MEASUREMENTS WITH A CONTACT IMPEDANCE CORRECTION

TECHNICAL FIELD

The present invention generally relates to the field of imaging through electrical measurements and more particularly, that of electrical impedance tomography.

The electrical impedance tomography (EIT) is a non-invasive imaging technique, which aims at reconstructing the internal distribution of electrical properties of a zone of a medium to be imaged from electrical measurements performed at its surface or on its perimeter.

The electrical impedance tomography has been originally used in the field of geophysics (where it is better known as "electrical resistivity tomography") and more particularly in oil, mine or hydrological exploration. It has then be applied to the non-destructive control where it is called "electrical resistance tomography" or "electrical capacitance tomography" depending on whether it aims at reconstructing the electrical conductivity or electrical permittivity of the medium. Finally, the electrical impedance tomography has been successively applied to the medical field as from the 1990's. It has been used in particular for the monitoring of lung ventilation and brain function (detection and monitoring of epileptic seizures), study of the gastro-intestinal tract function, and breast cancer screening. In spite of its low spatial resolution, EIT has developed in recent years because of its low cost, its non-intrusive and non-ionising character, its high time resolution as well as its contribution in characterising biological tissues and fluids.

The electrical impedance tomography presupposes that a plurality of electrodes are available at the surface of the zone of interest of the medium to be imaged. These electrodes allow, on the one hand, an electrical signal and thus an electric field to be applied in the medium in question and, on the other hand, the response of the medium to the signal thus applied to be collected.

FIG. 1 schematically represents an experimental electrical impedance tomography device.

The experimental device is herein, by way of illustration, a cylinder, represented herein in a cross-section view, delimiting a zone of interest.

At the surface of the zone of interest, 100, are provided N electrodes $110_1, 110_2, 110_3, \ldots, 110_N$ (here N=14). It has been supposed in the illustrated example that the zone of interest comprises a cylindrical anomaly 120. A current is injected in the medium (alternatively, a voltage difference is applied to this medium) using two electrodes, then the voltage difference (the current respectively) is measured between any pairs of electrodes. In the illustrated example, a current is injected in the medium by means of electrodes $100_8$ and $100_{11}$, and the voltage differences are measured between the electrodes $100_1$ and $100_2$, then $100_2$ and $100_3$, and so on. In the figure, the current lines are represented by 130 and the equipotential lines by 140.

From the voltages (or currents) thus measured, a mapping of an electrical variable, for example admittivity (complex conductivity), conductivity, permittivity or even impedivity or resistivity in the zone of interest can be deduced and imaged. It is reminded that the admittivity $\tilde{\sigma}$ of a medium can be written as:

$$\tilde{\sigma} = \sigma + j\omega \in_0 \in_r = 1/\tilde{z} \quad (1)$$

where $\sigma$ is the conductivity of the medium, $\in = \in_r \in_0$ is the permittivity of the medium ($\in_0$ is the vacuum electrical permittivity and $\in_r$ is the relative permittivity or even the dielectric constant of the medium) and $\tilde{z}$ is the impedivity of the medium.

Generally, it can be attempted to reconstruct the equivalent of an electrical variable such as a quantity, or a concentration, of a component of the medium being investigated, the electrical properties of which are known. For example, a conductivity value can be easily converted into an equivalent quantity of a known material having this conductivity. As a misuse of language, the electrical variable will designate hereinafter commonly used electrical variables (impedivity, conductivity, permittivity, admittivity) as well as their equivalents.

FIG. 2 represents the schematic diagram of a first electrical impedance tomography method known in the state of the art.

This method, called an absolute EIT method, involves the resolution of a so-called "direct" problem and a second so-called "inverse" problem.

The direct problem uses a meshing of the zone to be imaged. It consists in determining (analytically or by a numerical simulation), from a discrete distribution hypothesis of the electrical variable in the zone of interest, the signals collected by the different electrodes (as voltage differences or current intensities).

The inverse problem consists in deducing the mapping of the electrical variable of the zone of interest from the actually observed signals, that is the signals measured using electrodes.

More precisely, the impedance tomography method represented in FIG. 2 comprises a first step 210 of injecting a current in the zone of interest by means of the electrodes and, responsively, measuring the voltage differences between these electrodes. The voltage differences thus experimentally measured can be ranked in a vector with a size N, called a measurement vector and noted $U^{meas}$, provided in step 220.

Conversely, from a given spatial distribution, $\sigma$, of the electrical conductivity in the zone of interest, 230, ($\sigma$ is a vector with a size M where M is the number of meshes in the zone of interest), using a numerical model, called a direct model, the expected voltage differences can be calculated, in 240, when the abovementioned currents are injected. These voltage differences are arranged in 250 in a vector with a size N, called a calculated vector and noted $U^{calc}$.

The EIT method consists in searching for the spatial distribution of electrical conductivity (or generally the spatial distribution of an electrical variable) in the zone of interest which minimizes a cost function representative of the deviation between the measured vector and the calculated vector, $\|U^{meas} - U^{calc}\|$. The cost function is calculated in step 260.

This search or resolution of the inverse problem is performed by successive iterations from an initial distribution $\sigma_0$. This initial distribution could have been estimated by another characterisation method or even be a mean electrical conductivity value in the zone of interest. Each iteration allows the estimation (a priori estimation) of the electrical conductivity to be refined at the different points of the zone and the estimation thus refined (a posteriori estimation) is used as a new a priori distribution for the next iteration. The electrical conductivity is updated in step 270.

A lot of algorithms can be used to perform this update, for example the Gauss-Newton algorithm. An exemplary resolution of the inverse problem is described in the article by L.

M. Heikkinen et al. entitled "Simultaneous reconstruction of electrode contact impedances and internal electrical properties: II. Laboratory experiments" published in Meas. Sci. Techno. 13 (2002), pp. 1855-1861.

At the end of the iteration process (maximum number of iterations, convergence detection), the method provides an estimation of the electrical conductivity distribution a in the zone considered.

FIG. 3 represents a second impedance tomography method known in the state of the art. Unlike the first one, this one does not aim at obtaining an estimation of the electrical conductivity in the zone of interest but simply its variation between two given instants or frequencies. For this reason, it can be referred to as a differential EIT method.

From the same experimental device, currents with a given intensity are injected into a zone of interest, in steps 310, 315 corresponding to two different instants or two different frequencies. The current are injected by means of the electrodes and the voltage differences resulting therefrom are measured by means of these electrodes. The measured vectors $U_1^{meas}$ and $U_2^{meas}$ the elements of which are the voltage differences thus measured are respectively deduced in 320, 325.

In step 330, a cost function representative of the deviation $\|U_1^{meas} - U_2^{meas}\|$ between both measurement vectors is calculated and the electrical conductivity variation distribution, $\delta\sigma$, leading to this variation in the cost function is searched for in 340.

To do so, the cost function is linearized about the point of coordinates $(\hat{\sigma}_1, U_1^{meas})$ from the direct model, 350, where $\hat{\sigma}_1$ is the conductivity estimated in the previous step.

The electrical conductivity $\hat{\sigma}_2$ allowing the linearization during the next measurement is obtained by $\hat{\sigma}_2 = \hat{\sigma}_1 + \delta\sigma$. However, this estimation is herein relatively coarse and is only used for the purposes of linearization. As in the absolute EIT method, the initial reference $\sigma_0$ can be obtained by another characterisation method or even be a mean electrical conductivity value in the zone of interest.

The differential EIT method only allows the change in the impedance mapping to be estimated between two different instants or between two different frequencies. It is less sensitive than the absolute EIT method to the systematic measurement artefacts. Furthermore, it does not require the position of the electrodes to be known with as high an accuracy as for the absolute EIT method.

An exhaustive description of the differential EIT method (in time and frequency) can be found in the book by J. K. Seo and E. J. Woo entitled "*Nonlinear inverse problems in imaging*" Chap. 7.10-7.11, edited by J. Wiley & Sons.

Whatever the type of EIT method, being absolute or differential, the voltage differences (respectively currents) in response to a current injection (respectively a voltage application) can be measured according to different measurement configurations.

FIG. 4A represents a first measurement configuration for the implementation of a EIT method.

This first configuration, called a two-point configuration, is particularly simple since the measurement only involves two electrodes $E_1$ and $E_2$. A current i is injected in the medium by means of these two electrodes and the voltage difference u is measured between these same electrodes by means of an operational amplifier. The latter theoretically has an infinite impedance and thus a zero input current which does not disturb the measurement. On the other hand, as represented in the bottom of the figure, the contact impedances of the electrodes $E_1$ and $E_2$, respectively designated by $Z_{E_1}$ and $Z_{E_2}$, introduce a bias in the measurement because of the voltage drops occurring across their terminals. The voltage difference which is measured between the electrodes $E_1$ and $E_2$ is thus not representative of the voltage difference between the points $P_1$ and $P_2$ of the medium. Furthermore, this measurement error is a function of the injection current and the frequency. It is particularly high for small size electrodes (micro-EIT is then evoked) since the contact impedance increases when the contact area of the electrode in the medium decreases. In practice, the contact impedances for small size electrodes can be higher than the impedance of the medium located between two electrodes.

FIG. 4B represents a second configuration of electrodes for the implementation of an EIT method.

This second measurement configuration, called a four-point configuration, involves four electrodes, $E_1$ to $E_4$, two electrodes $E_1, E_2$ being used for injecting the current in the medium and two electrodes $E_3, E_4$, distinct from the first ones, being used for measuring the voltage difference, in response to this injection.

In this configuration, the input impedance of the operational amplifier being supposed as infinite, no current flows in the contact impedances $Z_{E_3}$ and $Z_{E_4}$ and, consequently, the voltage difference u measured between the electrodes $E_3$ and $E_4$ is actually that present between the points $P_3$ and $P_4$ of the medium.

It is understood from FIGS. 4A and 4B that only the four-point measurement configuration enables the biases on the voltage differences due to the contact impedances to be dispensed with. However, for a given number of electrodes, the four-point measurement configuration can lead to too low a number of independent measurements and therefore, it is desirable to complete the data set by combining a two-point configuration and a four-point configuration. Indeed, the resolution of the inverse problem requires that a great number of independent measurements are available because of the high number of unknowns (M values of the discretized electrical variable) to be determined in the resolution of the inverse problem.

To obtain a great number of error-free measurements, the conventional method is to integrate in the direct model the contact impedances as further unknowns (in fact N further unknowns). The resolution of the inverse problem then implies the joint determination of the values of the electrical variable and the contact impedances.

A first joint determination method of the values of the physical variable (at different points of the discretized zone) and the contact impedances has been provided in the aforementioned article by L. M. Hekkinen as well in the associated article by T. Vilhunen entitled "Detection of faults in resistive coatings with an impedance-tomography-related approach" published in Meas. Sci. Technol. 13 (2002), pp. 865-872. However, this method assumes that the medium of the zone of interest is homogeneous, which hypothesis is rarely confirmed in practice, in particular for biomedical applications.

A second joint determination method of the values of electrical variable and the contact impedances has been provided in the article by G. Boverman et al. entitled "Methods for compensating for variable electrode contact in EIT" published in IEEE Trans. on Biomedical Engineering, vol. 56, No. 12, December 2009, pp. 2762-2772. This method comprises a first step in which two parameters are estimated according to a non-linear approach, namely a homogeneous equivalent conductivity and a mean contact impedance valid for all the electrodes, and a second step of estimating the conductivity values at each point as well as different contact impedances, by disturbance around the abovementioned parameters.

However, this method is only applicable in the case where the problem of determining the contact impedances can be actually decoupled from that of the electrical conductivity values. But, this hypothesis is not necessarily confirmed and, when it is, the joint determination method turns out to be particularly complex.

The purpose of the present invention is consequently to provide an EIT method, and more generally a method for imaging an electrical variable in a zone of interest of a medium, enabling, in a simple robust manner, errors due to the contact impedances of the electrodes to be dispensed with without detriment to the resolution in this zone of interest.

DISCLOSURE OF THE INVENTION

The present invention is defined by a method for determining the spatial distribution of an electrical variable in a zone of interest of a medium, said method comprising performing measurements of voltage differences between electrodes in said medium, each electrode having with this medium a unit contact area, characterised in that:

for each electrode, a contact impedance with said medium is estimated, said contact impedance being estimated by measuring the impedance between said electrode and a counter-electrode having with said medium a contact area substantially higher than said unit contact area;

the voltage differences are corrected from the voltage drops occurring in the respective contact impedances of said electrodes;

the values of the electrical variable, or a variation in the same are determined, at a plurality of points of said zone of interest, from the voltage differences thus corrected.

The invention also relates to a method for determining the spatial distribution of an electrical variable in a zone of interest of a medium, said method comprising performing measurements of voltage differences between electrodes contacting the same, each electrode having with this medium a unit contact area, characterised in that:

for each electrode, a contact impedance with said medium is estimated, said contact impedance being estimated by measuring the impedance between said electrode and a counter-electrode having with said medium a contact area substantially higher than said unit contact area;

the corrected direct model is constructed allowing said voltage differences to be obtained from a spatial distribution of the electrical variable in the zone of interest, or a variation in the same, the corrected direct model taking into account the voltage drops thus estimated in the contact impedances;

the values of the electrical variable, or a variation in the same are determined, at a plurality of points of said zone of interest, from the measurements of voltage differences and the corrected direct model.

Advantageously, the counter-electrode is formed by a subset of said plurality of electrodes, said subset not containing the electrode the contact impedance of which is measured, the electrodes of said subset being short-circuited by means of the single-output switch.

Alternatively, the counter-electrode can be a dedicated electrode located at a distance from the electrodes which is substantially higher than the mean distance between the same.

Advantageously, the contact impedance can be measured by means of an impedance spectroscopy.

The contact impedance is advantageously measured from an equivalent circuit model representing the electrode and the medium of the zone of interest, the contact impedance being that in the equivalent circuit allowing the closest impedance spectrum to that measured by said impedance spectroscopy to be obtained.

Said electrical variable can be chosen from conductivity, resistivity, permittivity, admittivity, impedivity of the medium, or a function of one of these electrical variables, an equivalent quantity of a material an electrical variable of which is known, or a function of this quantity.

According to a first alternative, the variation in the electrical variable is taken at two distinct instants.

According to a second alternative, the variation in the electrical variable is taken at two distinct frequencies.

In this case, said method can be a differential EIT method or an EIT method.

Advantageously, the measurements of voltage differences between electrodes are performed in a two-point configuration, a current being injected between two electrodes and a voltage difference being measured between these same electrodes.

Whatever the embodiment, an image of the electrical variable, or of its variation, in this medium, can be constructed from the previously determined values of the electrical variable.

BRIEF DESCRIPTION OF DRAWINGS

Further characteristics and advantages of the invention will appear upon reading a preferential embodiment of the invention made in reference to the appended figures from which:

FIGS. 12A and 12B represent an EIT image of the zone of interest of a first and second media by means of an EIT method known in the state of the art;

FIGS. 13A and 13B represent an EIT image of this same zone of interest by means of an EIT method according to an exemplary embodiment of the invention.

DETAILED DISCLOSURE OF PARTICULAR EMBODIMENTS

In the following, an imaging method of an electrical variable in a zone of interest of a medium will be considered. The imaging method involves electrical measurements of this medium by means of a plurality of electrodes arranged at the surface of the same. In the following, we will assume, by way of illustration and without loss of generality, that the imaging method is an EIT method.

The idea underlying the invention is to determine the contact impedance of each electrode using a counter-electrode the area of which is substantially higher than the unit contact area between said electrode and the medium. The counter-electrode can be advantageously made by short-circuiting a subset of said plurality of electrodes not containing the electrode the contact impedance of which is to be measured.

First, an absolute EIT (or static EIT) method will be considered, given that the distribution of an electrical variable is estimated within a medium, as opposed to the differential EIT, where the distribution of the variation in an electrical variable is estimated within a medium.

Figure 5:
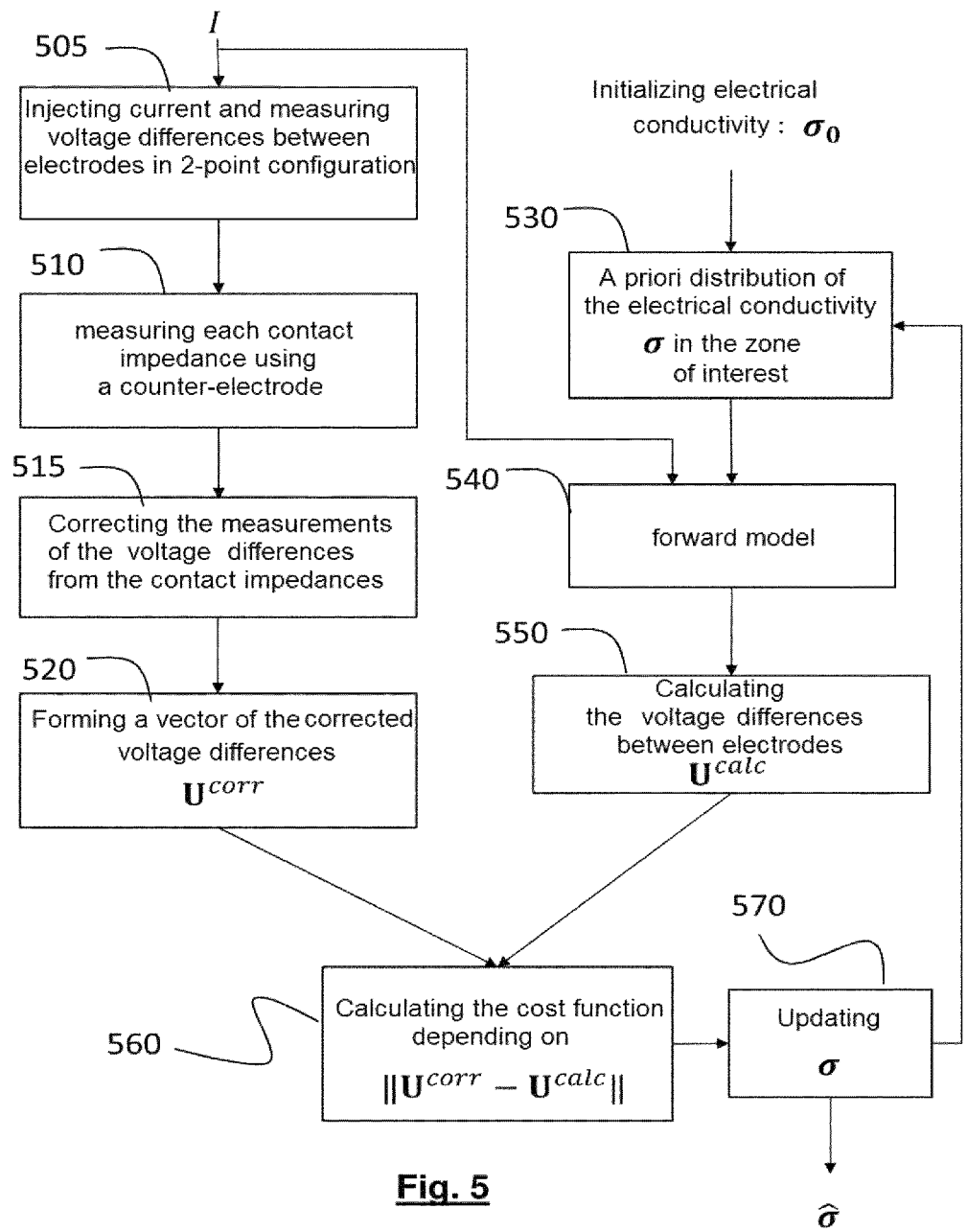
FIG. 5 schematically represents an imaging method of an electrical variable in a zone of interest, according to a first embodiment of the invention.

FIG. 5 schematically represents an imaging method of an electrical variable in a zone of interest, according to a first embodiment of the invention.

In step 505, a current is injected in the medium using a pair of electrodes and a voltage difference is measured between the same electrodes according to a 2-point measurement configuration. This operation is repeated for each pair of electrodes of said plurality of electrodes. More generally, a current can be injected in the medium using a first set of electrodes and the voltage differences between pairs of electrodes belonging to a second set of electrodes can be measured, the first and second sets of electrodes being not disjoint.

In step 510, the contact impedance of each electrode of said plurality of electrodes is measured. This measurement is performed using a counter-electrode placed in a single pole configuration, that is the presence of which has no influence on the distribution of the electrode field in the vicinity of the considered electrode. Theoretically, this corresponds to an electrode placed to infinity. In practice, an approximation of the single pole configuration is performed by taking, as a counter-electrode, an electrode having a contact area with the medium being substantially higher than the unit contact area of an electrode with this medium. For example, the contact area of the counter-electrode will be in the order of about ten or even several tens or several hundreds times higher than the unit contact area of a single electrode. According to a first alternative, the counter-electrode, CE, can be a dedicated electrode, distinct from the electrode used for the electrical measurements of the medium. In this case, the counter-electrode will be advantageously chosen distant from the latter. The mean distance between the electrodes and the counter-electrode can be in the order of about ten or about one hundred times the inter-electrode mean distance.

According to a second alternative, the counter-electrode is made by connecting together a subset of electrodes of said plurality of electrodes. More precisely, if $E_1, \ldots, E_N$ designates said plurality of electrodes and $E_i$ the electrode the contact impedance of which is desired to be determined, a subset $\Omega_i$ of electrodes $E_j$ is short-circuited, $j \neq i$, to make the counter-electrode CE. Preferably, the electrodes of the subset $\Omega_i$ are chosen distant from the electrode $E_i$, in the meaning defined above.

The purpose of the choice of a distant dedicated counter-electrode in the first alternative and a composite one in a second alternative is to not influence the measurement of the contact impedance by the local distribution of the conductivity of the medium.

The measurement of the contact impedance of an electrode relies on a representation of the impedance between the electrode and the counter-electrode by means of an equivalent circuit an example of which is described later in connection with FIG. 10. Different more or less complex equivalent circuit models can be contemplated by those skilled in the art, according to the desired accuracy, and according to the nature of the electrode and biological tissues with which they are in contact, without departing from the scope of the present invention. In any case, the contact impedance is determined from an impedance spectroscopy. More precisely, the complex impedance between the electrode and the counter-electrode is measured at a plurality of frequencies. It is then possible to determine the respective impedances of the different elements of the equivalent circuit, and especially the contact impedance, such that the impedance spectrum of the equivalent circuit is closest to the impedance spectrum measured in the meaning of a certain metrics.

The impedance spectrum can be measured, either in a galvanostatic mode, by flowing a predetermined current between the electrode and the counter-electrode, and measuring the voltage across the same, or in a potentiostatic mode, by applying a predetermined voltage between the electrode and the counter-electrode, and measuring the voltage flowing from one to the other.

Whatever the measurement mode used, step 510 provides contact impedances of the different electrodes. It should be noted that the order of steps 505 and 510 is immaterial.

In step 515, the voltage differences measured in step 505 are corrected from the contact impedances measured in step 510 and the value of the injected current. More precisely, if $u_{ij}$ is the voltage difference between the electrodes $E_i$ and $E_j$, and if $Z_e^i$ and $Z_e^j$ are the respective contact impedances of the electrodes $E_i$ and $E_j$, the corrected value $u_{ij}^{corr}$ of the voltage difference between these electrodes is:

$$u_{ij}^{corr} = u_{ij} - (Z_i^e + Z_j^e)I \tag{2}$$

where I is the intensity of the injected current. When necessary, the intensity of the injected cut can be chosen different depending on the pairs of electrodes considered, in which case:

$$u_{ij}^{corr} = u_{ij} - (Z_i^e + Z_j^e)I_{ij} \tag{3}$$

In step 520, the vector $U^{corr}$ of the voltage differences thus corrected is formed. The vector $U^{corr}$ is of a size $$\frac{N(N-1)}{2}, \text{ with } \frac{N(N-1)}{2} \geq M.$$

Figure 1:
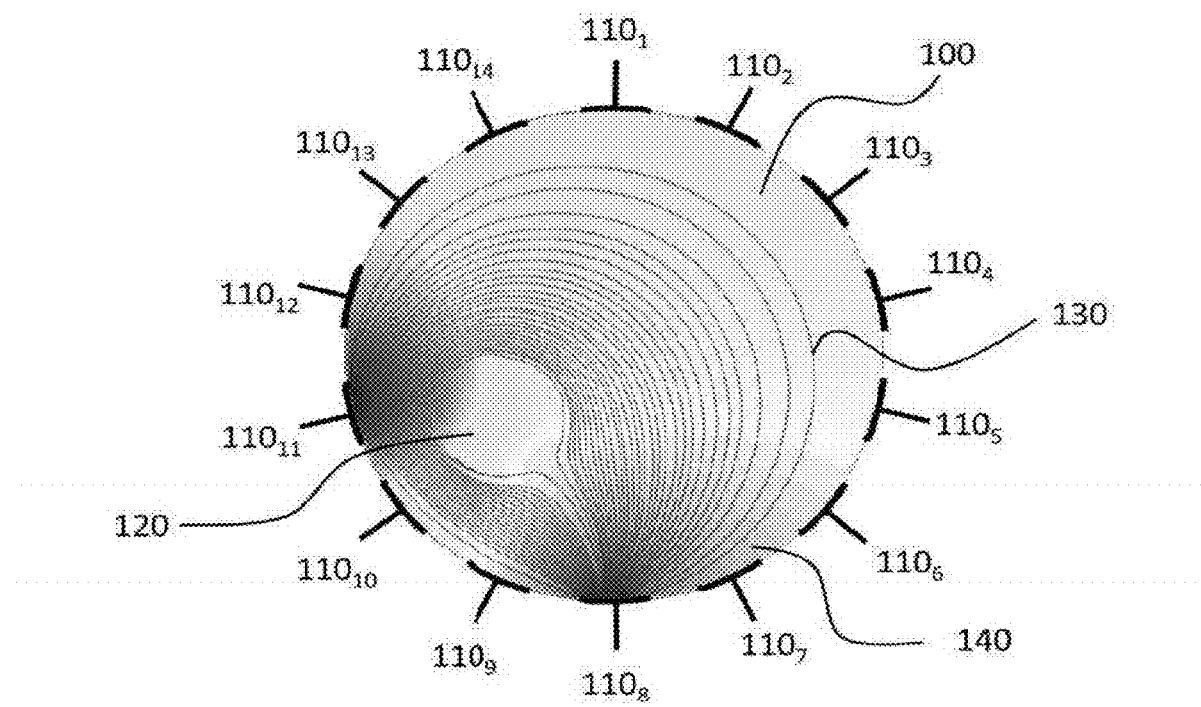
FIG. 1 schematically represents an experimental electrical impedance tomography device, known in the state of the art.
Figure 2:
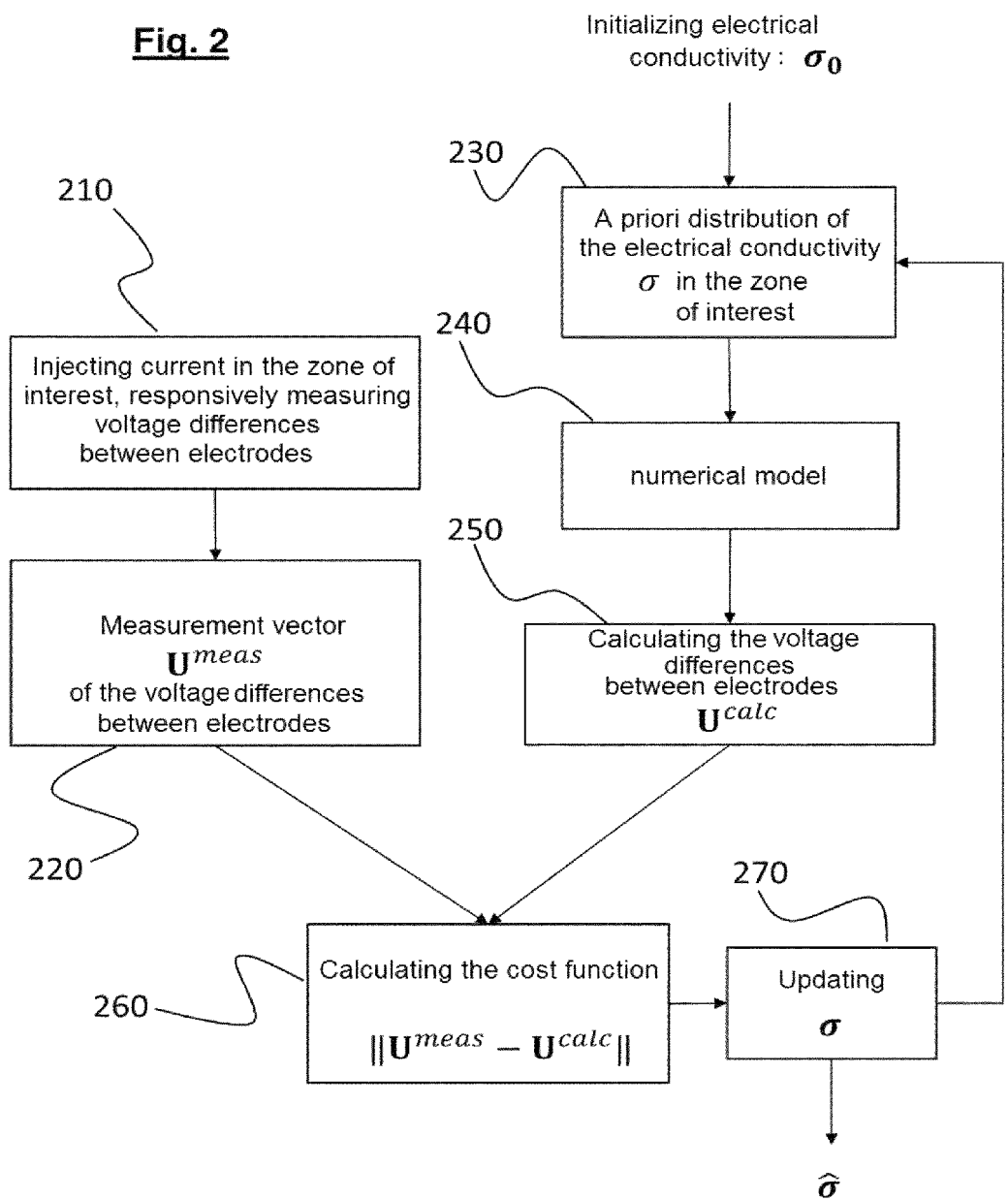
FIG. 2 represents the schematic diagram of a first electrical impedance tomography method known in the state of the art.

On the other hand, similarly to FIG. 2, from an a priori estimation of the distribution of the electrical conductivity in the zone of interest, 530, and from a numerical model (direct model) of the zone of interest, 540, a calculation of the expected voltage differences is made between the different electrodes, 550. This calculation is performed by injecting in the direct model the intensity of the injected current (or depending on the case, the intensities of the injected currents) during the measurement in step 505. The voltage differences thus calculated are ranked in a vector $U^{calc}$.

In 560, a cost function is then calculated depending on the deviation between the vector of the voltage differences calculated and the vector of the voltage differences corrected. This cost function can also comprise a regularisation term being the function of the deviation between the estimated distribution of the conductivity, $\hat{\sigma}$ and a reference distribution, $\sigma^{ref}$.

The estimation of the distribution of the conductivity is iteratively updated, in 570, from an initial distribution, $\sigma_0$, so as to minimise the cost function, for example:

$$f_h(\hat{\sigma}) = \frac{1}{2}\left(\|U^{corr} - U^{calc}\|^2 + h^2\|\hat{\sigma}\|^2\right) \quad (4)$$

This update can be performed by means of a conventional Gauss-Newton or Newton-Raphson algorithm, in a known manner per se.

Thus, for each iteration l, the conductivity in step l+1 is determined by:

$$\sigma^{l+1} = \sigma^l + \delta\sigma^l \quad (5\text{-}1)$$

Where the increment $\delta\sigma^l$ is determined by:

$$\delta\sigma^l = (J^T J + h^2 R)^{-1} J^T \delta U \quad (5\text{-}2)$$

where $\delta U = U^{corr} - U^{calc}$, R is a regularization matrix, for example the identity matrix, J is the Jacobean matrix of U with respect to $\sigma$ and h is an hyperparameter which controls the compromise between the term related to the data and the regularisation term in the cost function.

Those skilled in the art can complete or adapt this approach, for example taking into account weighting matrices on data and space, and contemplate other approaches for estimating parameters not implementing the Jacobean matrix J, for example analytical methods or D-bar-type methods.

The thus estimated conductivity distribution in the zone of interest can then be represented as an image.

Figure 6:
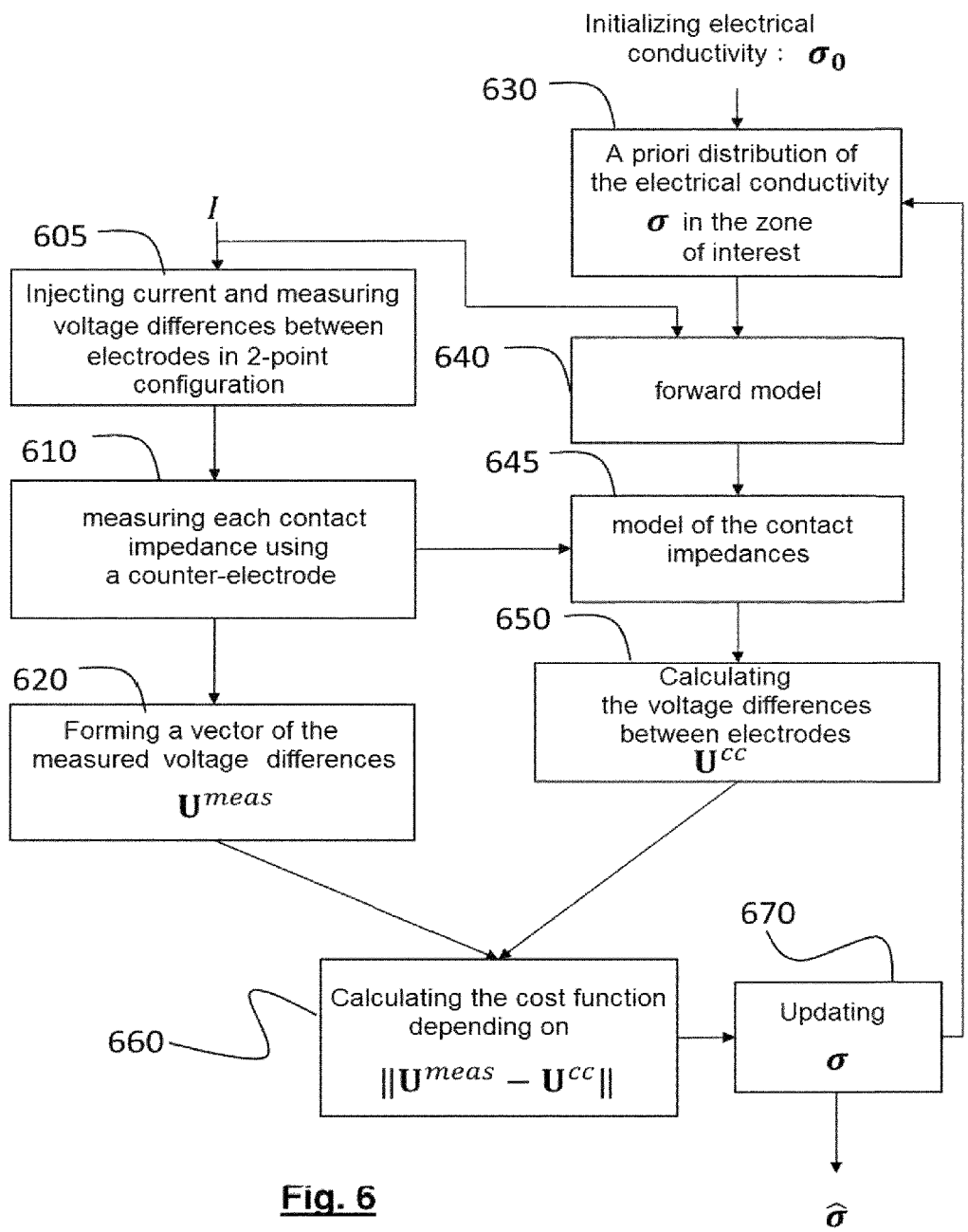
FIG. 6 schematically represents an imaging method of an electrical variable in a zone of interest, according to a second embodiment of the invention.

FIG. 6 schematically represents an imaging method of an electrical variable in a zone of interest, according to a second embodiment of the invention.

Unlike the previous embodiment, the voltage differences are not corrected from the voltage drops in the electrodes during the measurement but this correction is taken into account in the direct model.

Steps 605 and 610 are respectively identical to previously described steps 505 and 510. Besides, the contact impedances measured in 610 are not used herein to correct the measured voltage differences but are transmitted to step 645 to correct the direct model. The voltage difference measurements are arranged without a correction in a vector noted $U^{meas}$.

Similarly, steps 630 and 640 are respectively identical to steps 530 and 540. The voltage differences from the direct model are corrected in 645 by means of the contact impedances measured in step 610. More precisely, if the voltage differences calculated using the direct model are noted $u_{ij}^{calc}$, the voltage differences corrected by taking into account the contact impedances are obtained by:

$$u_{ij}^{cc} = u_{ij}^{calc} - (Z_i^e + Z_j^e)I \quad (6)$$

The voltage differences thus corrected are ranked in a vector $U^{cc}$ in 660.

The spatial distribution of the conductivity in the zone of interest is then estimated by means of an iterative process aiming at minimising a cost function, 660, depending on the deviation $\|U^{meas} - U^{cc}\|$ between the measured voltage differences and those calculated by taking into account the correction due to the contact impedances. As in the first embodiment, the spatial distribution of the conductivity thus estimated can be represented as an image.

According to an alternative not represented, the direct model integrates the contact impedances, in another words the values of these impedances are parameters of the model in the same way as the values of the electrical conductivity in the different meshes of the zone of interest. In this case, it will be understood that steps 640 and 645 are therefore merged.

The distribution of the conductivity thus estimated in 670 in the zone of interest can then be represented as an image.

Figure 7:
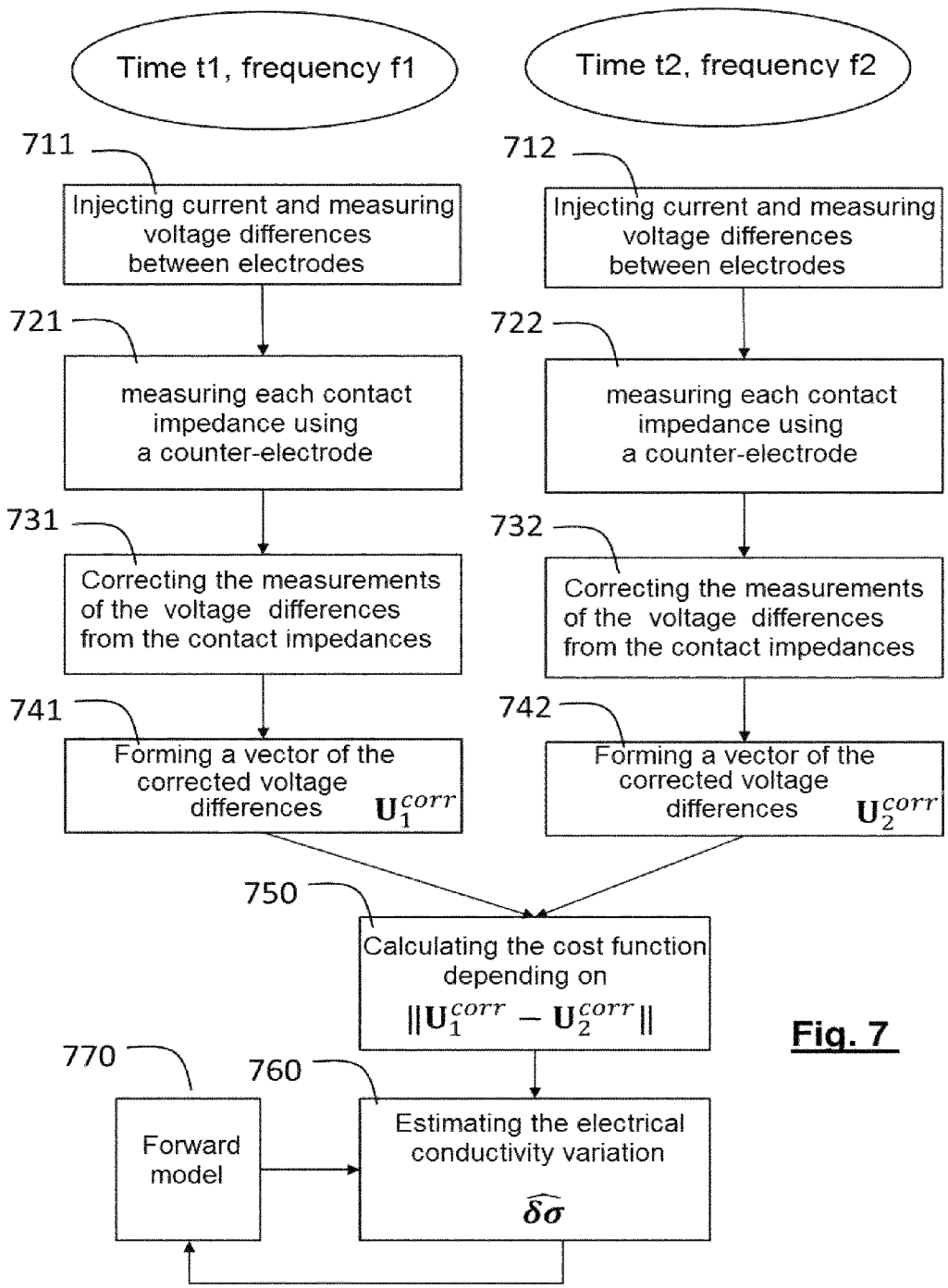
FIG. 7 schematically represents an imaging method of an electrical variable in a zone of interest, according to a third embodiment of the invention.

FIG. 7 schematically represents an imaging method of an electrical variable in a zone of interest, according to a third embodiment of the invention.

This embodiment relates for example to a differential EIT method.

At a time $t_1$ (or at a frequency $f_1$), in 711, a current injection is made between two electrodes and the voltage difference between the same electrodes is measured. This operation is repeated for each pair of electrodes.

Then in step 721, the contact impedance for each of these electrodes is measured (at time $t_1$ or at the frequency $f_1$). This measurement is made as in steps 510 and 610, using a large area counter-electrode with respect to a unit contact area of an electrode or by short-circuiting a subset of electrodes not containing the electrode the contact impedance of which is desired to be measured.

In step 731, the voltage differences measured in step 711 are corrected by means of the contact impedances determined in step 721. The thus corrected voltage differences are ranked in a first vector $U_1^{corr}$.

Steps 711-714 are repeated at a second instant $t_2$ or at a second frequency $f_2$, respectively in steps 712-742. In particular, it is understood that the contact impedances are also measured at the second instant or this second frequency. The measurements of the corrected voltage differences are ranked in a second vector $U_2^{corr}$.

In step 750, the value of a cost function depending on the deviation $\|U_1^{corr} - U_2^{corr}\|$ between the first vector of the corrected measurements and the second vector of the corrected measurements is determined. It is thus understood that the variations in the voltage differences are free from the contribution due to the variation in the contact impedances between both instants or both frequencies.

Figure 3:
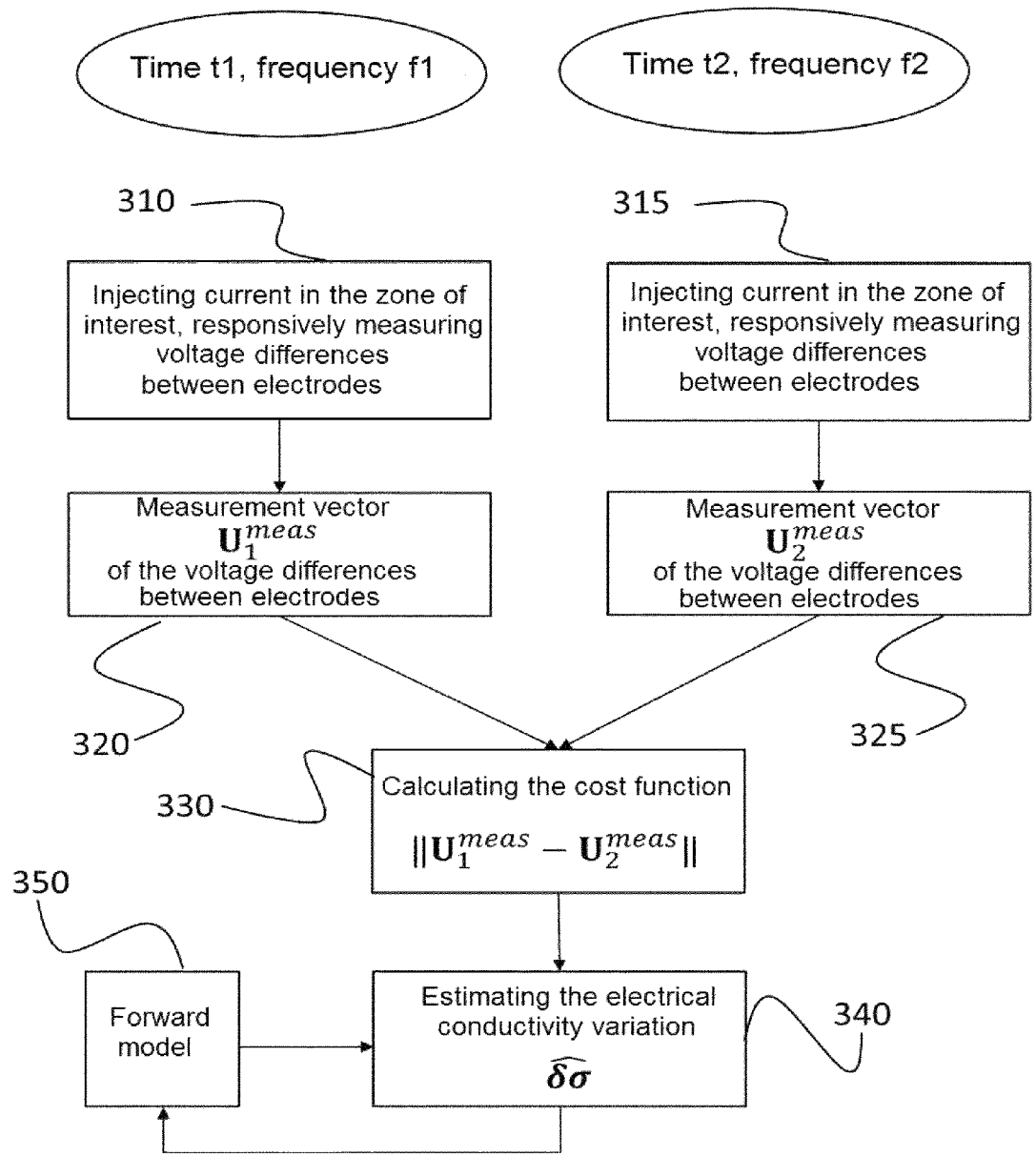
FIG. 3 represents the schematic diagram of a second electrical impedance tomography method known in the state of the art.
Figures 4A, 4B:
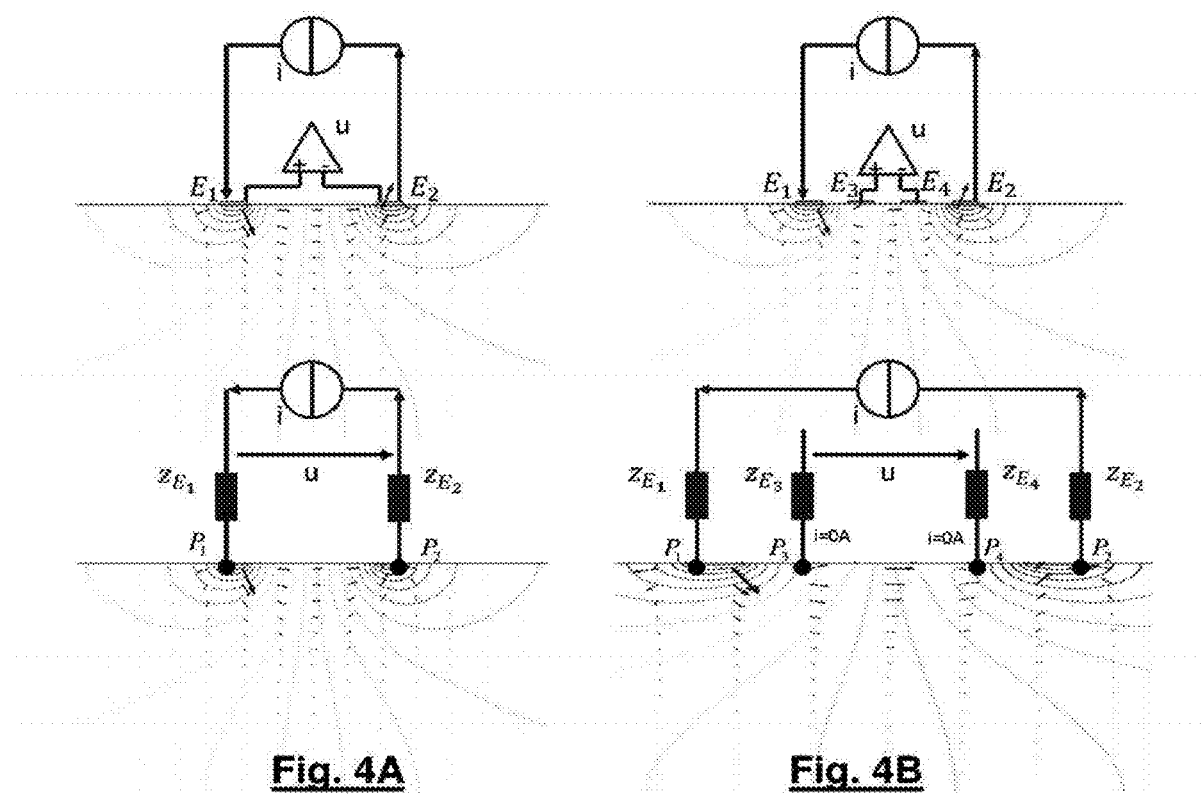
FIGS. 4A and 4B represent two measurement configurations for an EIT method.

As in step 340 of the differential EIT method in FIG. 3, a cost function is linearized about the point of coordinates $(\hat{\sigma}_1, U_1^{corr})$ from the direct model, 770, where $\hat{\sigma}_1$ is the conductivity estimated in the previous step. The conductivity variation $\widetilde{\delta\sigma}$ is obtained in 760 from the linearized cost function and the reference conductivity distribution $\hat{\sigma}_1$ is updated by $\hat{\sigma}_2 = \hat{\sigma}_1 + \delta\sigma$ for the application of the direct model.

The conductivity variation between two instants or two frequencies for the differential EIT can be determined by $\delta\sigma = (J^T J + h^2 R)^{-1} J^T \delta U$ où $\delta U = U_2^{corr} - U_1^{corr}$ for this embodiment of the invention.

Those skilled in the art can complete or adapt this approach, for example for taking into consideration weighting matrices on the data and space, and contemplate other approaches for estimating parameters which do not implement the Jacobean matrix J, for example analytical methods or D-bar methods.

The spatial distribution of the conductivity variation can then be represented as an image in the zone of interest.

Figure 8:
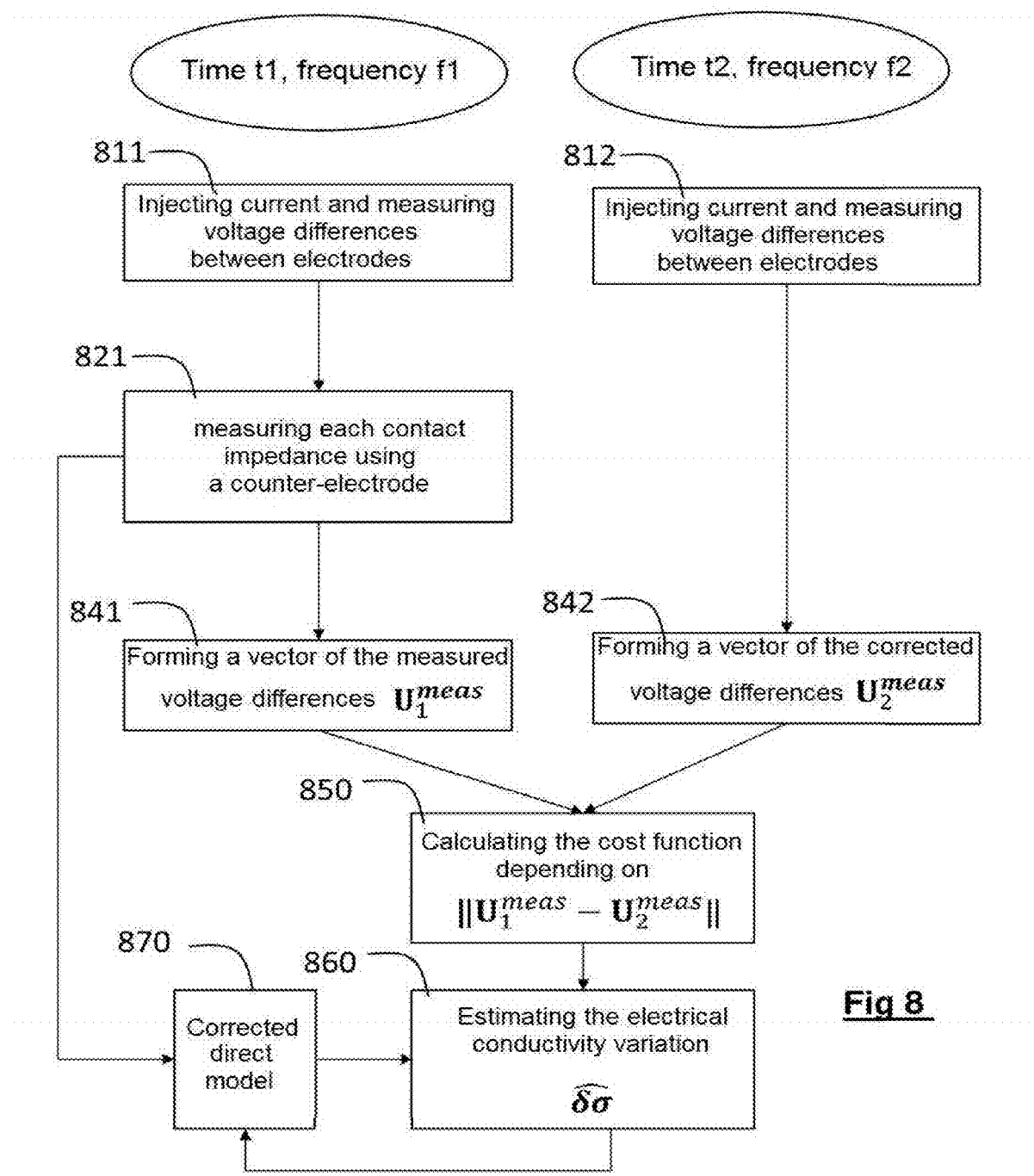
FIG. 8 schematically represents an imaging method of an electrical variable in a zone of interest, according to a fourth embodiment of the invention.

FIG. 8 schematically represents an imaging method of an electrical variable in a zone of interest, according to a fourth embodiment of the invention.

This embodiment is, as the previous one, of the differential type in that at two consecutive instants, or for two different frequencies, a current injection and a measurement of voltage difference are performed for each pair of electrodes, by means of the 2-point configuration. Steps 811 and 812 are identical to steps 711 and 712 of FIG. 7. At the first instant, or for the first frequency, a measurement of the contact impedances of the electrodes is performed in 821, in the same way as in step 721.

However, in the present embodiment, the measurements of the voltage differences are not corrected from the voltage drops in the contact impedances. The voltage differences at the first instant/first frequency and at the second instant/second frequency are respectively ranked in 841 and 842 in the vectors $U_1^{meas}$ and $U_2^{meas}$.

In step 850, the value of a cost function depending on the deviation $\|U_1^{meas}-U_2^{meas}\|$ is determined between the first vector of the corrected measurements and the second vector of the corrected measurements. This cost function is linearized about the point $(\hat{\sigma}_1, U_1^{meas})$, from the corrected direct model, 870, to take into account the contact impedances determined in step 821.

Thus, in 860, the spatial distribution of the electrical conductivity variation is determined in the zone of interest, $\widehat{\delta\sigma}$. This spatial distribution can be represented as an image in the zone of interest.

Figure 9:
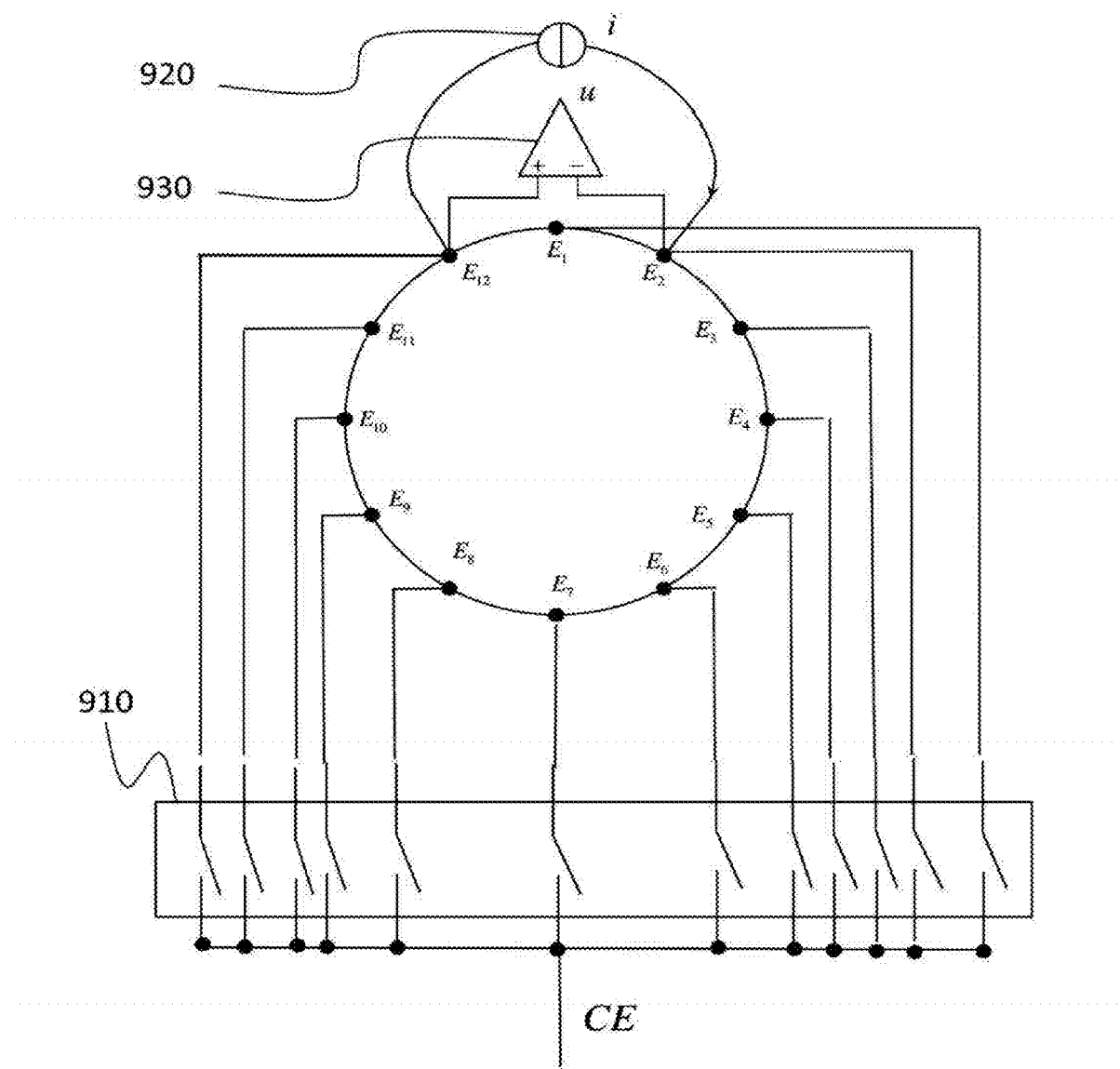
FIG. 9 schematically represents a system enabling contact impedances to be measured for the imaging method according to the invention.

FIG. 9 represents a system allowing the measurement of contact impedances for the embodiments of the invention illustrated in FIGS. 5-8. In other words, this system can be used in steps 510, 610, 721-722 and 821. The different electrodes $E_i$, i=1, . . . , N, are connected to a switch, 910, having N inputs and a common output CE, each input can be switched on the common output or not.

When a measurement of voltage difference u is made between two electrodes $E_i$ and $E_j$, these electrodes are connected to the terminals of a current generator 920 injecting a current i in the medium. The voltage difference u is measured using an operational amplifier 930. In this measurement mode, the inputs of the switch 910 are disconnected from the common output.

On the other hand, when the contact impedance of an electrode $E_i$ is desired to be measured, a subset $\Omega_i$ of electrodes of $\Omega$ not containing $E_i$ is chosen. The electrodes of $\Omega_i$ are preferably chosen distant from $E_i$, for example such that their distance from $E_i$ is in the order of about ten to several tens times the mean distance between neighbouring electrodes. The electrodes of $\Omega_i$ are connected to the common output CE whereas the electrodes of $\Omega \backslash \Omega_i$ are not connected thereto. The current generator 920 is connected to the electrode $E_i$ on the one hand and to the common output of the switch CE on the other hand. Further, the input terminals of the operational amplifier 930 are also connected to $E_i$ and CE. The impedance of an equivalent circuit consisting of the contact impedance of the electrode $E_i$ in series with the impedance of the medium is thus measured.

Figure 10:
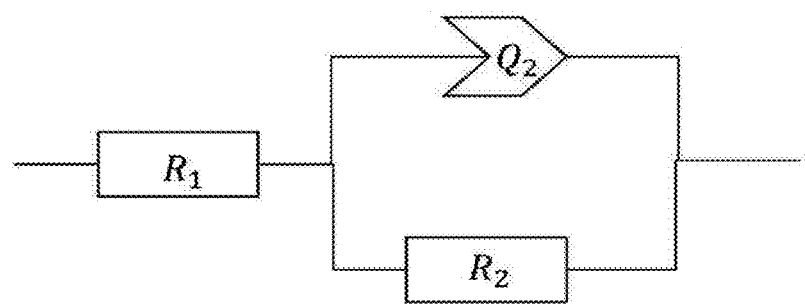
FIG. 10 schematically represents an electrical circuit equivalent to a contact impedance.

FIG. 10 represents an example of equivalent circuit modelling the impedance between an electrode and the counter-electrode CE.

In this example, the equivalent circuit is obtained by connecting in series a first resistor $R_1$, modelling the behaviour peculiar to the medium in the high frequency part of the spectrum (frequencies higher than 50 kHz) and of the contact impedance of the electrode, describing the interface phenomena in the low frequency part of the spectrum (frequencies lower than 10 KHz).

The contact impedance can be modelled by a second resistor $R_2$ in parallel with a constant phase element with the parameters $Q_2$ and $\alpha_2$. The contact impedance at the angular frequency $\omega$ is then $$Z_e(\omega) = \frac{R_2}{R_2 Q_2 (j\omega)^{\alpha_2} + 1}.$$

By making a measurement of the impedance spectrum between the electrode of interest and the counter-electrode, the values of the electrical elements of the equivalent circuit which make it possible to best approach the contact impedance of the electronic of interest can be found.

Figure 11:
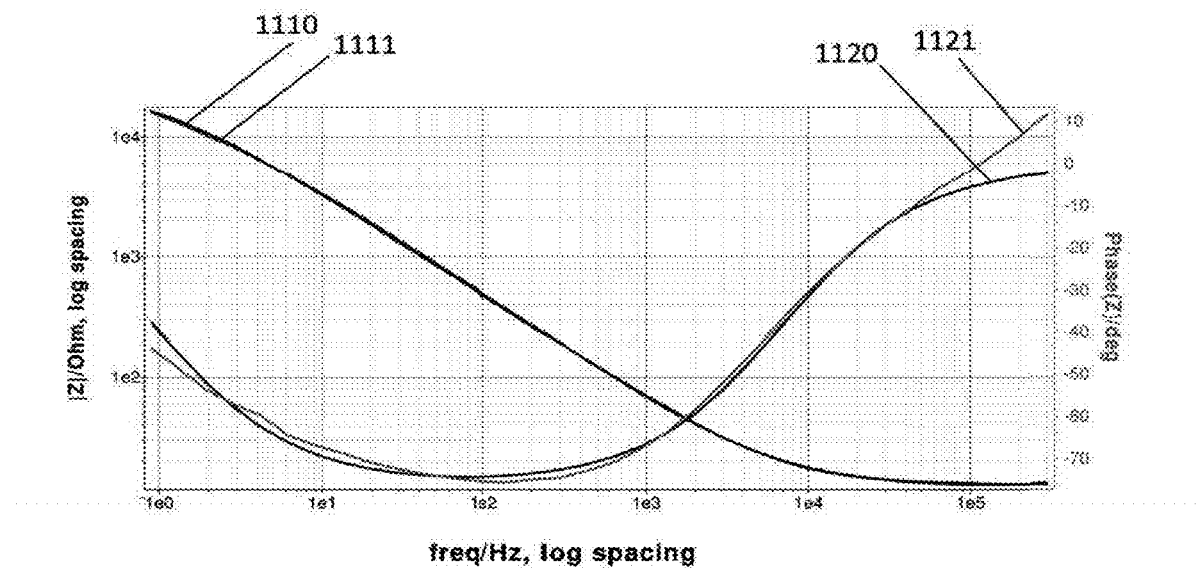
FIG. 11 represents as a Bode diagram an impedance spectrum of the equivalent circuit of FIG. 9 in connection with an impedance spectrum between an electrode and a counter-electrode.

For example, FIG. 11 represents according to a Bode diagram, the impedance spectrum measured between an electrode of interest and the counter-electrode (module in 1111 and phase in 1121) as well as the impedance spectrum of the equivalent circuit of FIG. 10, approaching as close as possible that measured (module of the impedance in 1110 and phase of the impedance in 1120). In particular, the elements $R_2$ and $Q_2$ modelling the contact impedance can thus be determined.

From the parameters of the model (herein $R_2$ and $Q_2$), the complex contact impedance is determined, or its module, or its phase, or its real part, or its imaginary part.

FIGS. 12A and 12B represent a frequency differential EIT image corresponding to different samples.

The sample of FIG. 12A has a conductivity distribution having a rotational symmetry about the centre axis of the sample.

The sample of FIG. 12B has a conductivity distribution off-centred with respect to the centre axis of the sample.

For both these samples, the differential EIT imaging method used involves measurements of voltage differences using a 4-point measurement configuration. The contact impedances are considered to be equal to an empirical value.

FIGS. 13A and 13B represent a frequency differential EIT image according to the third embodiment of the invention, for the same samples as those represented in FIGS. 12A and 12B.

The voltage differences have been measured in 2-point configuration, the same electrodes being used for injecting a current and measuring a voltage.

The contact impedances have been measured by impedance spectroscopy from the modelling of FIG. 10.

It is noted that the images of FIGS. 13A and 13B are better resolved than those of FIGS. 12A and 12B and have fewer artefacts. In particular, the off-centred conductivity zone in FIG. 13B is better isolated from the edge of the zone of interest.

Therefore, the invention provides an alternative to the state of the art for taking into account the contact impedances in the EIT process. All the electrodes can thus be used for acquiring data, since the link between measurements and data is properly made. Thereby, this increases the number of independent available measurements at a set number of electrodes. In particular, this makes it possible to implement measurement configurations in which at least one of the electrodes injecting a current in the medium being investigated is used to perform a voltage difference measurement. Thereby, the reliability of the reconstruction is improved.

The invention claimed is:

1. A method for determining the spatial distribution of an electrical variable in a zone of interest of a medium, said method comprising:
    performing measurements of voltage differences between electrodes in said medium, each electrode having with this medium a unit contact area,
    estimating, using processing circuitry and for each electrode, a contact impedance with said medium, said contact impedance being estimated by measuring the impedance between said electrode and a counter-electrode having with said medium a contact area substantially higher than said unit contact area;
    correcting the voltage differences from the voltage drops occurring in the respective contact impedances of said electrodes;
    determining, using the processing circuitry, the values of the electrical variable, or a variation in the same, at a plurality of points of said zone of interest, from the voltage differences thus corrected.

2. The method for determining the spatial distribution of an electrical variable according to claim 1, wherein the counter-electrode is formed by a subset of said plurality of electrodes, said subset not containing the electrode the contact impedance of which is measured, the electrodes of said subset being short-circuited by means of a single-output switch.

3. The method for determining the spatial distribution of an electrical variable according to claim 1, wherein the counter-electrode is a dedicated electrode at a distance from the electrodes which is substantially higher than the mean distance between the latter.

4. The method for determining the spatial distribution of an electrical variable according to claim 1, wherein the contact impedance is measured by means of an impedance spectroscopy.

5. The method for determining the spatial distribution of an electrical variable according to claim 4, wherein the contact impedance is measured from an equivalent circuit model representing the electrode and the medium of the zone of interest, the contact impedance being that in the equivalent circuit allowing the closest impedance spectrum to that measured by said impedance spectroscopy to be obtained.

6. The method for determining the spatial distribution of an electrical variable according to claim 1, wherein said electrical variable is chosen from conductivity, resistivity, permittivity, admittivity, impedivity of the medium, or a function of one these electrical variables, an equivalent quantity of a material an electrical variable of which is known, or a function of this quantity.

7. The method for determining the spatial distribution of an electrical variable according to claim 1, wherein the variation in the electrical variable is taken at two distinct instants.

8. The method for determining the spatial distribution of an electrical variable according to claim 7, comprising a differential EIT method.

9. The method for determining the spatial distribution of an electrical variable according to claim 1, wherein the variation in the electrical variable is taken at two distinct frequencies.

10. The method for determining the spatial distribution of an electrical variable according to claim 1, comprising an EIT method.

11. The method for determining the spatial distribution of an electrical variable according to claim 1, wherein the measurements of voltage differences between electrodes are performed in a two-point configuration, a current being injected between two electrodes and a voltage difference being measured between those same electrodes.

12. The method for determining the spatial distribution of an electrical variable according to claim 1, wherein an image of the electrical variable, or of its variation, in this medium, is constructed from the previously determined values of the electrical variable.

13. A method for determining the spatial distribution of an electrical variable in a zone of interest of a medium, said method comprising:
    performing measurements of voltage differences between electrodes contacting the same, each electrode having with this medium a unit contact area,
    estimating, using processing circuitry and for each electrode, a contact impedance with said medium, said contact impedance being estimated by measuring the impedance between said electrode and a counter-electrode having with said medium a contact area substantially higher than said unit contact area;
    constructing a corrected direct model allowing said voltage differences to be obtained from a spatial distribution of the electrical variable in the zone of interest, or a variation in the same, the corrected direct model taking into account the voltage drops thus estimated in the contact impedances;
    determining, using the processing circuitry, the values of the electrical variable, or a variation in the same, at a plurality of points of said zone of interest, from the measurements of voltage differences and the corrected direct model.

* * * * *

UNITED STATES PATENT AND TRADEMARK OFFICE
CERTIFICATE OF CORRECTION

PATENT NO. : 9,933,380 B2  Page 1 of 1
APPLICATION NO. : 14/953153
DATED : April 3, 2018
INVENTOR(S) : Alexandre Fouchard et al.

It is certified that error appears in the above-identified patent and that said Letters Patent is hereby corrected as shown below:

On the Title Page

Item (71), the Applicants' Information is incorrect. Item (71) should read:
-- (71) Applicants: Commissariat a L'Energie Atomique et aux Energies Alternatives, Paris (FR); Institut National de la Sante et de la Recherche Medicale (INSERM), Paris Cedex 13 (FR) --

Signed and Sealed this
Sixteenth Day of April, 2019

Andrei Iancu
*Director of the United States Patent and Trademark Office*